United States Patent [19]

Ishikawa et al.

[11] 4,370,447
[45] Jan. 25, 1983

[54] UNSATURATED POLYESTER RESIN COMPOSITIONS

[75] Inventors: Katuhiro Ishikawa; Ryotaro Ohno; Masatoshi Arakawa, all of Yokkaichi, Japan

[73] Assignee: Japan Synthetic Rubber Co., Ltd., Tokyo, Japan

[21] Appl. No.: 253,832

[22] PCT Filed: Jul. 18, 1980

[86] PCT No.: PCT/JP80/00163
§ 371 Date: Mar. 11, 1981
§ 102(e) Date: Mar. 11, 1981

[87] PCT Pub. No.: WO81/00258
PCT Pub. Date: Feb. 5, 1981

[30] Foreign Application Priority Data
Jul. 19, 1979 [JP] Japan ................... 54-90957

[51] Int. Cl.³ .............. C08G 63/76; C08L 67/00
[52] U.S. Cl. ........................ 525/39; 525/35; 525/36; 525/38; 525/40
[58] Field of Search ............ 525/35, 36, 40, 38, 525/39; 528/86, 298

[56] References Cited
U.S. PATENT DOCUMENTS
2,757,160  7/1963  Anderson ............... 525/35
3,714,291  1/1973  Rockey .................. 525/35

Primary Examiner—Jacob Ziegler
Attorney, Agent, or Firm—Oblon, Fisher, Spivak, McClelland & Maier

[57] ABSTRACT

An unsaturated polyester was obtained by reacting a polyhydric alcohol with a mixture of an unsaturated polybasic acid and a specific saturated dibasic acid represented by the formula:

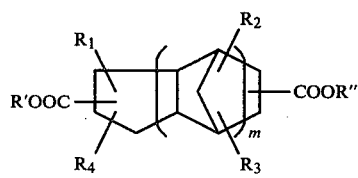

or the formula:

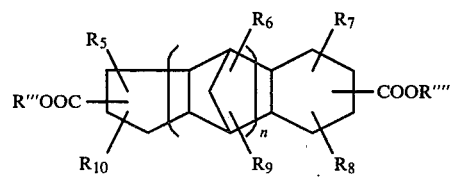

wherein, $R_1$ to $R_{10}$ are each hydrogen or alkyl, $R'$ to $R''''$ are the same or different and each represent hydrogen or ester-exchangeable alkyl, m is 1 or 2, and n is zero or 1. The compositions comprising this polyester and an aromatic vinyl monomer, when hardened in the presence of a catalyst, exhibit a lower shrinkage during the hardening and give molded products with improved resistance to alkalis and to boiling water.

21 Claims, No Drawings

UNSATURATED POLYESTER RESIN COMPOSITIONS

TECHNICAL FIELD

The present invention relates to novel unsaturated polyester resin compositions.

BACKGROUND ART

Unsaturated polyester resins, which are produced by hardening unsaturated polyesters obtained by polycondensation of unsaturated polybasic acid component and saturated polybasic acid component with polyhydric alcohol components (hereinafter, said unsaturated polyesters are referred to simply as unsaturated polyesters), with $\alpha,\beta$-ethylenically unsaturated monomers in the presence of a catalyst, have many advantageous characteristics, that is, relatively low costs of materials available for manufacture, ease of molding, excellent physical properties of hardened products, and no hazard of poisonous solvent because of the needlessness of solvent for application, and they have therefore various applications as molding materials. In particular, they are currently used widely as leading plastics available in combination with glass fiber for fiberglass reinforced plastics (FRP), which enjoy demands tending to increase year after year, as structural materials for boats at large, fishing boats, bathtubs, tanks, pipes, etc.

While having such various advantages, unsaturated polyester resins also have disadvantages, among which high shrinkage during hardening and poor alkali resistance have been pointed out. This shrinkage is not only a significant drawback for molding applications where high dimensional precision is required, but also a cause of cracks due to the increased internal strain, and further it presents the problem of deteriorating the resin adhesion to glass fiber. Secondly, unsaturated polyester resins are susceptible to acid- or base-promoted hydrolysis, particularly to erosion by alkaline solutions because high-molecular structure thereof is constructed through ester bonds. This has been a serious problem in application fields of unsaturated polyester resins. In addition, requirements for water resistance are getting more and more strict from the user side.

In order to prevent the shrinkage of unsaturated polyester resin during hardening, addition of a thermoplastic polymer thereto has so far been practiced, but this prior technique has many drawbacks and limited applications because the two polymers are incompatible with each other. As chemical-resistant unsaturated polyester resins, there have been known those which employ isophthalic acid as an acid component or employ bisphenol A or hydrogenated bisphenol A as a polyhydric alcohol component. Such polyester resins, though resistant to alkaline solutions, are liable to develop a milky turbidity because of the poor compatibility with the $\alpha,\beta$-ethylenically unsaturated monomer jointly used, and the molded products tend to crack because they are too hard.

DISCLOSURE OF THE INVENTION

The object of this invention is to provide novel unsaturated polyester resin compositions having improved resistance to chemicals and to boiling water and minimized shrinkage during hardening.

This invention provides unsaturated polyester resin compositions comprising (A) an unsaturated polyester and (B) an $\alpha,\beta$-ethylenically unsaturated monomer component containing an aromatic vinyl monomer, said unsaturated polyester being obtained from (i) acid components consisting:

of an unsaturated polybasic acid and at least one of specific saturated dibasic acids or esters thereof, or of an unsaturated polybasic acid and a mixture of said dibasic acid or ester thereof with another saturated polybasic acid, and from (ii) a polyhydric alcohol component containing at least one member selected from the group consisting of ethylene glycol, propylene glycol, neopentyl glycol, and bisphenol A derivatives, and said specific saturated dibasic acids or esters thereof being represented by the formula:

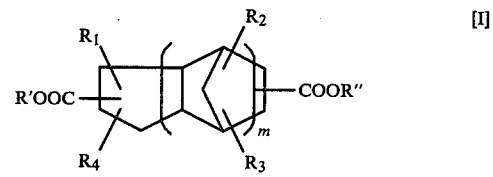

($R_1$ to $R_4$ are each hydrogen or alkyl, $R'$ and $R''$ are the same or different and each represent hydrogen or ester-exchangeable alkyl, and m is 1 or 2), or the formula:

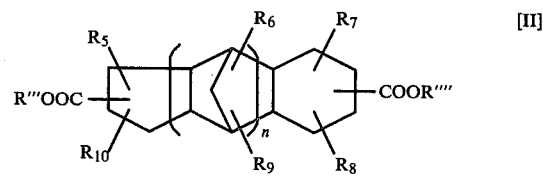

($R_5$ to $R_{10}$ are each hydrogen or alkyl, $R'''$ and $R''''$ are the same or different and each represent hydrogen or ester-exchangeable alkyl, and n is zero or 1).

The primary characteristic of this invention is that all or part of the saturated polybasic acid component to be used for preparing the unsaturated polyester is replaced by one or more of the saturated dibasic acids of formula [I] or [II].

$R'$, $R''$, $R'''$, and $R''''$ in formulas [I] and [II] and each alkyl, when not hydrogen, that can undergo ester exchange reaction in the polyester synthesis, and this alkyl usually has 1 to 3 carbon atoms. Thus, $R'$, $R''$, $R'''$, and $R''''$ are desirable to be each hydrogen or $C_1$–$C_3$ alkyl. On the other hand, $R_1$ to $R_{10}$ are each hydrogen or alkyl, and with respect to alkyl they are not particularly restricted, but usually they may be $C_1$–$C_3$ alkyls.

The second characteristic of this invention is that at least one member selected from the group consisting of ethylene glycol, propylene glycol, neopentyl glycol, and bisphenol A derivative is used as all or part of the polyhydric alcohol component, and the third characteristic is that the $\alpha,\beta$-ethylenically unsaturated monomer component contains an aromatic vinyl monomer as the essential ingredient.

BEST MODE FOR CARRYING OUT THE INVENTION

The unsaturated polyester resin compositions of this invention, unlike the conventional compositions, are markedly improved in the resistance to alkalis and to boiling water and in dimentional stability by introducing the specific saturated dibasic acid represented by the above formulas as a saturated polybasic acid component, and alkali resistance thereof further improved by use of the above specified compound as a polyhydric alcohol component is superior to those of isophthalic acid type, isophthalic acid-special glycol type, and bisphenol type unsaturated polyester resin compositions which are conventionally used as corrosion-resistant plastic. In addition to this, the compositions of this invention are distinguished by easy handling owing to the better thickening properties, and giving to the cured products higher heat distortion temperature as well as good flexibility. Thus, the compositions of this invention are excellent as unsaturated polyester resin compositions for producing molded articles. They are best processed by laminate molding, cast molding, or press molding.

The saturated dibasic acids represented by formula [I] or [II], which are used for the novel unsaturated polyester resin compositions of this invention as a saturated polybasic acid component, can be readily obtained by the so-called hydroesterification which comprises reacting carbon monoxide and water or an alcohol upon a corresponding alicyclic diene such as dicyclopentadiene or tetrahydroindene.

For example, the following dibasic acids or esters are favorably used:

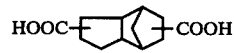
dicarboxytricyclo[5,2,1,0$^{2,6}$]decane

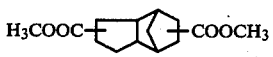
di(methoxycarbonyl)tricyclo[5,2,1,0$^{2,6}$]decane

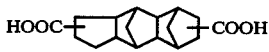
dicarboxypentacyclo[6,5,1,1$^{3,6}$, 0$^{2,7}$, 0$^{9,13}$]pentadecane

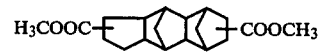
di(methoxycarbonyl)pentacyclo[6,5,1,1$^{3,6}$, 0$^{2,7}$, 0$^{9,13}$]-pentadecane

dicarboxydicyclo[4,3,0$^{2,6}$]nonane

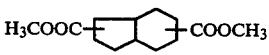
di(methoxycarbonyl)dicyclo[4,3,0$^{2,6}$]nonane

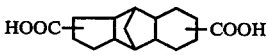
dicarboxytetracyclo[6,5,1,0$^{2,7}$,0$^{9,15}$]tetradecane

di(methoxycarbonyl)tetracyclo[6,5,1,0$^{2,7}$,0$^{9,15}$]-tetradecane The other saturated polybasic acids used, as required, in combination with these alicyclic saturated dibasic acids include aromatic polycarboxylic acids such as phthalic anhydride, isophthalic acid, terephthalic acid, trimellitic acid, pyromellitic acid, naphthalenedicarboxylic acids; aliphatic polycarboxylic acids such as succinic acid, adipic acid, azelaic acid, sebacic acid; tetrahydrophthalic acid (including its anhydride), endomethylenetetrahydrophthalic acid (including its anhydride), Het Acid (chlorendic acid), and alkyl esters of all these acids wherein each alkyl is an ester-exchangeable one customarily used.

The saturated dibasic acid represented by formula [I] or [II] is used in an amount not less than 5 mol %, preferably 50 mol % or more, based on the total amount of the saturated polybasic acids used, whereby the dimensional stability, alkali resistance, and boiling water resistance of the compositions are markedly improved.

The unsaturated polybasic acids adapted for use in combination with these dibasic acids include maleic anhydride, maleic acid, fumaric acid, itaconic acid, etc. The suitable molar ratio of the saturated polybasic acid to the unsaturated polybasic acid ranges from 10:90 to 80:20.

In this invention, the polyhydric alcohol component to react with the above acid components for producing the unsaturated polyester require to consist all or partly of at least one glycol selected from ethylene glycol, propylene glycol, neopentyl glycol, and bisphenol A [2,2-bis(4'-hydroxyphenyl)propane] derivatives such as hydrogenated bisphenol A and propylene glycol adducts of bisphenol A. Additionally, a common polyhydric alcohol such as 1,4-cyclohexanediol, 1,4-butanediol, 1,4-cyclohexanedimethanol, glycerol, or pentaerythritol may be partly used as occasion demands. The above specified glycol is used preferably in an amount not less than 50 mol % of the total amount of polyhydric alcohols used.

The molecular weight of the unsaturated polyester obtained from the above-mentioned components is desirable to be a proper value in the order of 1,000 to 10,000 so as to permit the subsequent molding or hardening to be carried out without trouble and to enable the molded products to maintain satisfactory physical properties. For this purpose, the amount ratio of the acid components to the polyhydric alcohol component used for producing the unsaturated polyester is desirably 1:1.1 to 1:1.02 in terms of the ratio of total carboxyl equivalent to total hdyroxyl equivalent. When an alicyclic compound represented by formula [I] or [II] is used in the form of free acid, the unsaturated polyester can be obtained in the ordinary way used in the polycondensation reaction of a free polybasic acid with a polyhydric alcohol, and when the alicyclic compound is used in the form of ester, the unsaturated polyester can be obtained in a similar way but in the presence of the ordinary catalyst for ester-exchange reaction.

The aromatic vinyl monomer which is essential to the unsaturated polyester resin compositions of this invention includes styrene, ring-substituted chlorostyrenes, ring-substituted bromostyrenes, α-methylstyrene, vinyltoluene and divinylbenzene, which are used each alone or in combination with one another. If necessary, other common vinyl monomers such as vinyl acetate, acrylic acid, methacrylic acid, acrylic acid esters, methacrylic acid esters, acrylonitrile, acrylamide, and diallylphthalate each can be used in combination with the above aromatic vinyl monomer. The content of the aromatic vinyl monomer is preferably not less than 50% by weight based on the total amount of the α,β-ethylenically unsaturated monomers, which can be used in a ratio to the unsaturated polyester of 90:10 through 10:90 by weight, preferably 60:40 through 20:80 by weight.

To the unsaturated polyester resin compositions, a common stabilizer such as hydroquinone, catechol, or benzoquinone may be added. The compositions thus obtained can be used for producing various kinds of molded articles by hardening them in the presence of a common catalyst through compounding, as occasion demands, with some materials selected from fillers, inorganic fibers such as glass fiber, boron fiber, and carbon fiber, organic fibers such as vinyl fiber and polyester fiber, thermoplastic polymers, releasing agents, flame retardants, ultraviolet absorbers, blowing agents, pigments, etc.

As the catalyst, a hardener is used in high temperature curing, and a suitable combination of a hardener with a hardening accelerator is used in ambient temperature curing. The suited hardners include benzoylperoxide, methyl ethyl ketone peroxide, cylohexanone peroxide, dicumyl peroxide, and t-butyl perbenzoate, and the suited accelerators include cobalt naphthenate, cobalt octenoate, manganese naphthenate, dimethylaniline, diphenyl disulfide, and quarternary ammonium salts.

The following examples and referrence example illustrate the present invention in more detail and are, however, not to be construed to limit the scope of the invention.

Properties of the molded samples in the examples, i.e., color number, water absorption, boiling water absorption, alkali resistance, Barcol hardness, heat distortion temperature, coefficient of volume shrinkage, flexural strength after boiling water immersion test, and flexural elastic modulus after the same test were measured in accordance with JIS K-6901. The appearance was determined by visual evaluation. Of these properties, the coefficient of volume shrinkage was expressed by the following equation:

Coefficient of volume shrinkage (%) =

$$\frac{\text{(Specific gravity of hardened resin)} - \text{(Specific gravity of liquid resin)}}{\text{Specific gravity of hardened resin}}$$

wherein the specific gravity of hardened resin was measured in accordance with JIS K-6911, and the specific gravity of liquid resin in accordance with JIS K-6901.

REFERENCE EXAMPLE 1

Synthesis of Dicarboxytricyclo[5,2,1,0$^{2.6}$]decane

A 2-liter autoclave provided with an induction stirrer was loaded with 268 g (2.0 mol) of dicyclopentadiene, 160 g (5.0 mol) of methanol, 158 g (2.0 mol) of pyridine, and 171 g (0.5 mol) of dicobalt octacarbonyl, sufficiently purged with gaseous nitrogen, and filled with carbon monoxide gas to a pressure of 100 Kg/cm$^2$ at room temperature. Subsequently, the autoclave was heated to 110° C. to carry reaction for 3 hours, and the temperature was raised to 140° C. to continue the reaction for further 3 hours till the absorption of carbon monoxide ceased. Thereafter, the autoclave was cooled and unreacted carbon monoxide was discharged. The reaction mixture was taken up in 1 liter of cyclohexane under an atmosphere of nitrogen, freed from the catalyst, washed with an acid and then with water, distilled to remove cyclohexane, and subjected to vacuum distillation to obtain 300 g of a fraction having a boiling range of 120°-130° C./1 mmHg. The saponification value of the compound obtained was 435 (the theoretical saponification value of dicarboxymethyltricyclo[5,2,1,0$^{2.6}$]decane is 445).

Subsequently, the compound obtained was converted into the potassium salt by reaction at 80° C. with an aqueous solution containing an equivalent amount or more of potassium hydroxide, and then unsaponified compound was removed with ether. A free carboxylic acid was obtained by adding 10% hydrochloric acid to acidify the resulting liquid. The acid value of the compound obtained was 498, which is in agreement with a value of 500 of dicarboxytricyclo[5,2,1,0$^{2.6}$]-decane. It was confirmed by gel permeation chromatography and NMR and IR spectrography that the structure of the compound is as the following formula:

EXAMPLE 1

A 1-liter, four-necked flask fitted with a stirrer, a gas inlet tube, a thermometer, and a fractionating condenser was loaded with 2.1 mol of propylene glycol, 1.0 mol of maleic anhydride, and 1.0 mol of dicarboxytricyclo[5,2,1,0$^{2.6}$]decane, and the mixture was subjected to condensation reaction at 160°-210° C. under a stream of nitrogen to give an acid value of 30, whereby an unsaturated polyester was synthesized. Subsequently, unsaturated polyester resin composition (I) of good compatibility was prepared by mixing 70 parts by weight of the resulting unsaturated polyester with 30 parts by weight of styrene containing 0.01 part by weight of hydroquinone.

EXAMPLE 2

A 1-liter, four-necked flask fitted with a stirrer, a gas inlet tube, a thermometer, and a fractionating condenser was loaded with 2.1 mol of propylene glycol, 1.0 mol of di(methoxycarbonyl)tricyclo-[5,2,1,0$^{2.6}$]decane, and 1.0 g of zinc acetate as ester-exchange catalyst. The mixture was reacted at 190°-230° C. under a stream of nitrogen until the theoretical amount of methanol had been distilled out. Then, 1.0 mol of maleic anhydride was added, and the mixture was subjected to condensation reaction at 180°-210° C. to give an acid value of 8, whereby an unsaturated polyester was synthesized.

Subsequently, unsaturated polyester resin composition (II) of good compatibility was prepared by mixing 70 parts by weight of the unsaturated polyester thus obtained and 30 parts by weight of styrene containing 0.01 part by weight of hydroquinone.

EXAMPLE 3

Unsaturated polyester resin composition (III) was obtained in the same way as in Example 1 except that dicarboxypentacyclo[6,5,1,1$^{3.6}$,0$^{2.7}$,0$^{3.9}$]pentadecane was used in place of dicarboxytricyclo[5,2,1,0$^{2.6}$]decane.

EXAMPLE 4

Unsaturated polyester resin composition (IV) was obtained in the same way as in Example 1 except that dicarboxytetracyclo[6,5,1,0$^{2.7}$,0$^{9.15}$]tetradecane was used in place of dicarboxytricyclo[5,2,1,0$^{2.6}$]decane.

Cast plates were prepared by adding 1% of benzoyl peroxide to respective unsaturated polyester resin compositions [I] to [IV] obtained in Examples 1 to 4 and heating the mixture at 80° C. for 1 hour and then at 120° C. for further 1 hour. Properties of these cast plates are shown in Table 1.

For the purpose of comparison, properties of the plates molded by use of phthalic anhydride-based unsaturated polyester resin composition (VIII) and by use of isophthalic acid-based unsaturated polyester resin composition (IX) are shown also in Table 1 as comparative examples. Composition (VIII) was prepared according to Example 1 from 2.1 mol of propylene glycol, 1.0 mol of phthalic anhydride, and 1.0 mol of maleic anhydride, and composition (IX) was prepared according to Example 1 from 2.1 mol of propylene glycol, 1.0 mol of isophthalic acid, and 1.0 mol of maleic anhydride.

of dicarboxytricyclo[5,2,1,0$^{2.6}$]decane, the component ratios of said mixtures being shown in Table 2. The compositions obtained are designated as unsaturated polyester resin compositions (V), (VI), and (VII), respectively.

TABLE 2

| | Unsaturated polyester resin composition No. | | |
|---|---|---|---|
| Saturated acid used | Example 5 (V) | Example 6 (VI) | Example 7 (VII) |
| Phthalic anhydride | 0.25 mol | 0.50 mol | 0.75 mol |
| Dicarboxytricyclo [5,2,1,0$^{0.5}$]decane | 0.75 mol | 0.50 mol | 0.25 mol |

TABLE 1

| | Unsaturated polyester resin composition No. | | | | | |
|---|---|---|---|---|---|---|
| | Example | | | | Comparative example | |
| Property | I | II | III | IV | VIII | IX |
| Color number (Gardner) | 2 | 1 | 2 | 2 | 1 | 1 |
| Barcol hardness | 32 | 31 | 35 | 36 | 34 | 33 |
| Water absorption (%) | 0.2 | 0.2 | 0.2 | 0.2 | 0.2 | 0.2 |
| Boiling water absorption (%) | 0.4 | 0.5 | 0.4 | 0.4 | 0.6 | 0.5 |
| Flexural strength retention (%)[a] | 83 | 80 | 75 | 69 | 52 | 68 |
| Flexural elasticity modulus retention (%)[a] | 100 | 100 | 100 | 98 | 83 | 97 |
| Appearance[b] | Excellent (no surface change) | Excellent (no surface change) | Excellent (no surface change) | Excellent (no surface change) | Fine cracks all over the surface | A few fine cracks |
| Heat distortion temperature (°C.) | 95 | 92 | 102 | 105 | 74 | 85 |
| Coefficient of volume shrinkage (%) | 6.3 | 6.4 | 6.0 | 6.0 | 7.7 | 7.3 |
| Alkali resistance (wt. loss %) Boiling time | | | | | | |
| 10 hr | 0 | 0 | 0 | 0 | 0.5 | 0 |
| 50 hr | 0 | 0 | 0 | 0 | 5.4 | 1.2 |
| 100 hr | 1.0 | 0.3 | 0.8 | 0.7 | 17.2 | 3.6 |
| 200 hr | 4.1 | 2.3 | 3.8 | 3.6 | 33.3 | 11.5 |
| 300 hr | 8.1 | 7.9 | 7.7 | 7.4 | 46.0 | 23.8 |
| 400 hr | 13.0 | 15.4 | 12.0 | 11.8 | 58.8 | 33.2 |

Note
[a]Value after immersion in boiling water (100° C.) for 100 hours.
Note
[b]Value after immersion in boiling water (100° C.) for 200 hours.

EXAMPLES 5 TO 7

Unsaturated polyester resin compositions were obtained by repeating the process of Example 1 except that mixtures of phthalic anhydride and dicarboxytricyclo[5,2,1,0$^{2.6}$]decane were each used in place of 1.0 mol Cast plates were prepared in the same way as in Examples 1 to 4 from unsaturated polyester resin compositions (V) to (VII) obtained in Examples 5 to 7. The results of tests on properties of the cast plates are shown in Table 3.

TABLE 3

| | | Unsaturated polyester resin composition No. | | | | | |
|---|---|---|---|---|---|---|---|
| | | Example | | | | Comparative example (the same as Table 1) | |
| | | I | V | VI | VII | VIII | IX |
| | | Saturated acid | | | | | |
| Property | *1PAn *2DCPA | 0 1 mol | 0.25 mol 0.75 mol | 0.50 mol 0.50 mol | 0.75 mol 0.25 mol | 1 mol 0 | (Isophthalic acid) |
| Color number (Gardner) | | 2 | 2 | 1 | 1 | 1 | 1 |
| Barcol hardness | | 32 | 38 | 37 | 36 | 34 | 33 |
| Water absorption (%) | | 0.2 | 0.2 | 0.2 | 0.2 | 0.2 | 0.2 |
| Boiling water absorption (%) | | 0.4 | 0.4 | 0.5 | 0.5 | 0.6 | 0.5 |
| Heat distortion temperature (°C.) | | 95 | 91 | 88 | 84 | 74 | 85 |
| Coefficient of volume shrinkage | | 6.3 | 6.4 | 6.6 | 7.0 | 7.7 | 7.3 |
| Alkali resistance (wt. loss %) Boiling time | | | | | | | |
| 10 hr | | 0 | 0 | 0 | 0.2 | 0.5 | 0 |
| 50 hr | | 0 | 0.4 | 1.0 | 1.5 | 5.4 | 1.2 |
| 100 hr | | 1.0 | 2.1 | 3.2 | 3.8 | 17.2 | 3.6 |
| 200 hr | | 4.1 | 6.6 | 8.8 | 10.3 | 33.3 | 11.5 |
| 300 hr | | 8.1 | 10.8 | 16.3 | 21.2 | 46.0 | 23.8 |

TABLE 3-continued

| | | Unsaturated polyester resin composition No. | | | | | |
|---|---|---|---|---|---|---|---|
| | | Example | | | | Comparative example (the same as Table 1) | |
| | | I | V | VI | VII | VIII | IX |
| | | | | Saturated acid | | | |
| Property | *¹PAn | 0 | 0.25 mol | 0.50 mol | 0.75 mol | 1 mol | (Isophthalic acid) |
| | *²DCPA | 1 mol | 0.75 mol | 0.50 mol | 0.25 mol | 0 | |
| 400 hr | | 13.0 | 16.2 | 24.8 | 31.5 | 58.8 | 33.2 |

*¹PAn: Isophthalic anhydride
*²DCPA: Dicarboxytricyclo[5,2,1,0$^{2.6}$]decane

As is obvious from the results of the examples and comparative examples, the unsaturated polyester resin compositions according to this invention have low volume shrinkage, high resistance to alkali and to boiling water, and additionally higher heat distortion temperatures as compared with those based on phthalic acid, hence providing excellent molded products. Particularly, when the alicyclic compound of this invention is used in an amount of 50 mol % or more, its effect on these properties is prominent.

EXAMPLE 8

Unsaturated polyester resin composition (X) was obtained by repeating the process of Example 1 except that hydrogenated bisphenol A was used in place of propylene glycol. The composition obtained was transparent.

On the other hand, unsaturated polyester resin composition (IX) (hydrogenated bisphenol A-isophthalic acid type) similarly prepared for comparison using 2.1 mol of hydrogenated bisphenol A, 1.0 mol of isophthalic acid, and 1.0 mol of maleic anhydride was milky turbid, i.e., inferior in transparency.

Table 4 shows results of tests on the cast plates prepared from compositions (X) and (XI) in the same way as in Examples 1 to 4.

TABLE 4

| Property | Example 8 (X) | Comparative example (XI) |
|---|---|---|
| Color number (Gardner) | 2 | Milky turbid |
| Barcol hardness | 35 | 33 |
| Water absorption (%) | 0.2 | 0.2 |
| Boiling water absorption (%) | 0.3 | 0.3 |
| Heat distortion temperature (°C.) | 127 | 122 |
| Coefficient of volume shrinkage (%) | 5.4 | 5.6 |
| Alkali resistance (wt. loss %) Boiling time | | |
| 100 hr | 0 | 0 |
| 200 hr | 0 | 0 |
| 400 hr | 0 | 0 |

We claim:
1. Unsaturated polyester resin compositions comprising (A) unsaturated polyesters prepared from unsaturated polybasic acid components, saturated polybasic acid components, and polyhydric alcohol components, and (B) $\alpha,\beta$-ethylenically unsaturated monomer components, which are characterized in that:
  (1) all or part of said saturated polybasic acid components consist of at least one of saturated dibasic acids or esters thereof represented by the formula:

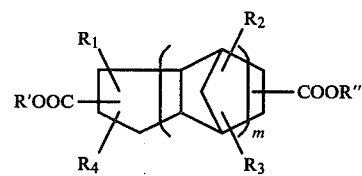

($R_1$ to $R_4$ are each hydrogen or alkyl, $R'$ and $R''$ are the same or different and each represent hydrogen or ester-exchangeable alkyl, and m is 1 or 2), or the formula:

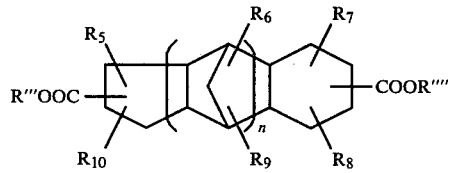

($R_5$ to $R_{10}$ are each hydrogen or alkyl, $R'''$ and $R''''$ are the same or different and each represent hydrogen or ester-exchangeable alkyl, and n is zero or 1),
  (2) all or part of said polyhydric alcohol components consist of at least one glycol selected from the group consisting of ethylene glycol, propylene glycol, neopentyl glycol, and bisphenol A derivatives, and
  (3) all or part of said $\alpha,\beta$-ethylenically unsaturated monomer components consist of an aromatic vinyl monomer.

2. Compositions of claim 1, wherein said saturated dibasic acids or esters thereof are represented by the formula:

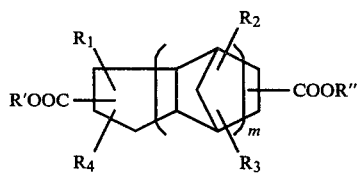

($R_1$ to $R_4$ are each hydrogen or alkyl, $R'$ and $R''$ are the same or different and each represent hydrogen or ester-exchangeable alkyl, and m is 1 or 2).

3. Compositions of claim 1, wherein said saturated dibasic acids or esters thereof are represented by the formula:

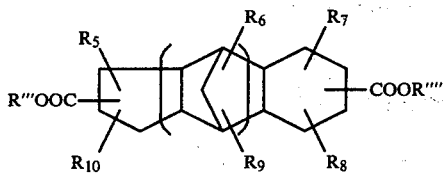

(R₅ to R₁₀ are each hydrogen or alkyl, R''' and R'''' are the same or different and each represent hydrogen or ester-exchangeable alkyl, and n is zero or 1).

4. Compositions of claim 1, 2 or 3, wherein the amount of the saturated dibasic acid or ester thereof used is not less than 5 mol % based on the total amount of the saturated polybasic acid components used.

5. Compositions of claim 4, wherein the amount of the saturated dibasic acid or ester thereof used is not less than 50 mol % based on the total amount of the saturated polybasic acid components used.

6. Compositions of claim 1, wherein the molar ratio of the saturated polybasic acid components used to the unsaturated polybasic acid components used ranges from 10:90 to 80:20.

7. Compositions of claim 1, wherein the amount of said glycol used is not less than 50 mol % based on the total amount of the polyhydric alcohol components.

8. Compositions of claim 1, wherein the bisphenol A derivative is hydrogenated bisphenol A or a propylene glycol adduct of bisphenol A.

9. Compositions of claim 1, wherein the saturated polybasic acid components are also selected from the group consisting of phthalic anhydride, isophthalic acid, terephthalic acid, trimellitic acid, pyromellitic acid, naphthalenedicarboxylic acids, succinic acid, adipic acid, azelaic acid, sebacic acid, tetrahydrophthalic acid, tetrahydrophthalic anhydride, endomethylenetetrahydrophthalic acid, endomethylenetetrahydrophthalic anhydride, chlorendic acid, and ester-exchangeable alkyl esters of all these acids.

10. Compositions of claim 1, wherein the unsaturated polybasic acid components are selected from the group consisting of maleic anhydride, maleic acid, fumaric acid, and itaconic acid.

11. Compositions of claim 1, wherein the polyhydric alcohol components are selected from the group consisting of 1,4-cyclohexanediol, 1,4-butanediol, 1,4-cyclohexanedimethanol, diethylene glycol, glycerol, and pentaerithritol.

12. Compositions of claim 1, wherein the molecular weights of said unsaturated polyesters are 1,000 to 10,000.

13. Compositions of claim 1, wherein said aromatic vinyl monomer is selected from the group consisting of styrene, ring-substituted chlorostyrenes, ring-substituted bromostyrenes, α-methylstyrene, vinyltoluene, and divinylbenzene.

14. Compositions of claim 1, wherein the α,β-ethylenically unsaturated monomer is selected from the group consisting of vinyl acetate, acrylic acid, methacrylic acid, acrylic acid esters, methacrylic acid esters, acrylonitrile, acrylamide, and diallyl phthalate.

15. Compositions of claim 1, wherein the amount of said aromatic vinyl monomer used is not less than 50% by weight of the total amount of the α,β-ethylenically unsaturated monomers.

16. Compositions of claim 1, wherein the weight ratio of the whole α,β-ethylenically unsaturated monomer to the unsaturated polyester ranges from 10:90 to 90:10.

17. Compositions of claim 16, wherein said weight ratio ranges from 60:40 to 20:80.

18. A process for producing unsaturated polyester resins which comprises hardening compositions of claim 1 in the presence of a catalyst.

19. Unsaturated polyester resins produced by a process of claim 18.

20. Unsaturated polyester resin molded articles produced in molds by a process of claim 18.

21. The compositions of claim 1 wherein all of the unsaturated polybasic acid components are represented by said cyclo compounds represented by the formulas.

* * * * *